United States Patent [19]

Reissenweber et al.

[11] Patent Number: 4,537,986
[45] Date of Patent: Aug. 27, 1985

[54] PREPARATION OF PYROCATECHOL METHYLCARBAMATE

[75] Inventors: Gernot Reissenweber, Boehl-Iggelheim; Siegfried Kersten, Frankenthal; Walter Ditter, Heidelberg; Peter Jacobs, Gruenstadt, all of Fed. Rep. of Germany

[73] Assignee: BASF Aktiengesellschaft, Fed. Rep. of Germany

[21] Appl. No.: 517,625

[22] Filed: Jul. 27, 1983

[30] Foreign Application Priority Data

Jul. 27, 1982 [DE] Fed. Rep. of Germany ........ 3227931

[51] Int. Cl.$^3$ .......................................... C07C 125/067
[52] U.S. Cl. .................................................... 560/132
[58] Field of Search .......................................... 560/132

[56] References Cited

U.S. PATENT DOCUMENTS 3,449,405  6/1969  Seto et al. ............................ 560/132
3,470,236  9/1969  Hausweiler et al. ................. 560/132
3,843,720  10/1974  Nikles .................................. 560/132

FOREIGN PATENT DOCUMENTS 2650828  5/1978  Fed. Rep. of Germany ...... 560/132

OTHER PUBLICATIONS

*Chemical Abstracts*, vol. 89, abstract No. 42781y, (1978), Loeffler et al., II.
Houben–Weyl, *Methoden der Organischen Chemie*, 3rd ed., vol. 8, pp. 139-140.
*Journal fur Praktische Chemie*, vol. 313, No. 4, (1971), p. 626, Ohme et al.
*Liebig's Ann. Chem.*, vol. 300, (1898), p. 135, Einhorn.
*Liebig's Ann Chem.*, vol. 562, (1949), p. 205, Petersen.
*Derwent Abstracts*, abstract No. 35128A (corresponds to German Offenlegungsschrift No. 2650828), Loeffler et al., I.

*Primary Examiner*—Michael L. Shippen
*Assistant Examiner*—Patricia M. Scott
*Attorney, Agent, or Firm*—Keil & Weinkauf

[57] ABSTRACT

Pyrocatechol methylcarbamate is prepared by reacting pyrocatechol carbonate with methylamine in the presence of a tertiary amine and, preferably, a solvent.

4 Claims, No Drawings

PREPARATION OF PYROCATECHOL METHYLCARBAMATE

The present invention relates to a process for the preparation of pyrocatechol methylcarbamate, an intermediate for certain crop protection agents, by reacting pyrocatechol carbonate with methylamine in the presence of a tertiary amine and, preferably, a solvent.

Processes for the preparation of pyrocatechol carbamates by reacting pyrocatechol carbonate with a primary or secondary amine are disclosed in, for example, Liebig's Ann. Chem. 300 (1898) 135; ibid. 562 (1949), 205, J. Prakt. Chem. 313 (1971), 626 and German Laid-Open Application DOS No. 2,650,828; cf. also Houben-Weyl, 4th edition, Volume 8, page 139/140.

The known processes have a number of disadvantages, especially for preparation on an industrially economical scale: the relatively sparingly soluble carbamates already precipitate from most of the conventional solvents during the reaction. The resulting suspensions can be conveyed only with difficulty, which complicates continuous preparation. Through mixing of the reactants and the removal of the heat of reaction are also particularly difficult, which leads to the formation of byproducts such as pyrocatechol and N,N'-dimethylurea. Although a solvent with better dissolving properties exists, i.e. acetone, large amounts of pyrocatechol are formed as a by-product when the reaction is carried out in acetone, since methylamine and acetone give the Schiff base in a pre-extended equilibrium and the water thereby liberated hydrolyzes the carbamate. Another suitable solvent, 1,4-dioxane, cannot be used for toxicological reasons.

We have found that, according to the invention, pyrocatechol methylcarbamate can be prepared by a smooth process if pyrocatechol carbonate is reacted with methylamine in the presence of a tertiary amine. The addition of the tertiary amine has two surprising consequences: on the one hand, the solubility of the carbamates is substantially increased, so that as much as 30% strength carbamate solutions are possible, for example, in methylene chloride, and on the other hand, the reaction proceeds substantially more rapidly than in the absence of the additive, according to the invention about four times more rapidly, so that a correspondingly better space/time yield is possible.

The reaction proceeds at a sufficient rate at from $-50°$ to $+50°$ C., preferably from $-20°$ to $20°$ C.

Chlorohydrocarbons, e.g. dichloromethane, dichloroethane and dichloroethylene, and so-called aproticpolar solvents, e.g. tetrahydrofuran, dimethylformamide and dimethyl sulfoxide, are used as the solvents, although the latter type are generally more expensive.

Any amine of the general formula $N(R)_3$, where R is a straight-chain or branched aliphatic or cycloaliphatic radical of, for example, not more than 15 carbon atoms, or two radicals R together are the ring members of a cyclic amine, can be used as the tertiary amine. The radicals R are identical or different. Examples of amines are triethylamine, tri-n-propylamine, tributylamine, triisobutylamine, tri-2-ethylhexylamine, N,N-dimethylethylamine, N,N-dimethylisopropylamine, N,N-dimethyl-2-ethylhexylamine, N-methylditridecylamine, dimethylcyclohexylamine, N-methyldicyclohexylamine and N-methylhexamethyleneimine. Quasi-aromatic amines, e.g. pyridine, are also suitable. The amount of tertiary amine added is advantageously from 0.05 to 2 moles, preferably from 0.2 to 1.4 moles, per mole of carbonate.

Advantageously, the pyrocatechol carbonate is initially taken in the chosen solvent together with the chosen tertiary amine, and the stoichiometric amount of methylamine, is added a little at a time, with vigorous thorough mixing. On an industrial scale, it is advantageous to react a solution of pyrocatechol carbonate and the tertiary amine continuously with methylamine in a circulation apparatus or in a reaction tube. The pyrocatechol carbonate and tertiary amine can also be fed in separately in solution, and reacted togetherr with methylamine.

The carbamate can be obtained from the reaction mixture by converting the tertiary amine into a salt and then isolating the carbamate, which crystallizes out. If necessary, the carbamate is freed from ammonium salts by washing with water. If the presence of the amine causes no trouble, the carbamate solutions themselves can be used immediately for further reaction steps, for example for alkylation of the free hydroxyl group.

A good yield of pyrocatechol methylcarbamate of high purity can be prepared by the process according to the invention. Precisely in this case is the preparation of very pure products of particular importance, since the carbamates prepared by the process according to the invention are useful intermediates for insecticidal active ingredients (German Published Application DAS No. 2,231,249).

EXAMPLE 1

155 g of gaseous methylamine were fed into a solution of 680 g of pyrocatechol carbonate and 555 g of triethylamine in 2.5 liters of methylene chloride at 5° C., with vigorous stirring. 500 g of 36% strength hydrochloric acid were then added and the product was filtered off with suction and washed with water. 801 g (96% of the expected amount) of pyrocatechol methylcarbamate of melting point 125° C. were obtained.

EXAMPLE 2

A solution of 1,088 g of pyrocatechol carbonate and 1,016 g of N,N-dimethylcyclohexylamine per 4 liters of methylene chloride was fed into a circulation apparatus of 180 ml capacity at a rate of 4.8 liters/hour, 198 g/hour of methylamine simultaneously being fed in via a second inlet. The temperature was kept at from 10° to 15° C. The solution flowing out of the apparatus was analyzed by high pressure liquid chromatography every 20 minutes; it was found that the conversion of pyrocatechol carbonate was complete and the pyrocatechol carbamate obtained was 96 to 98% pure. A total of 10 liters of a solution prepared in this manner were worked up as described above and gave 2,080 g (93%) of pyrocatechol methylcarbamate; content according to high pressure liquid chromatography: 99%.

We claim:

1. A process for the preparation of pyrocatechol methylcarbamate by reacting pyrocatechol carbonate with methylamine, wherein the reaction is carried out in the presence of 0.2 to 1.4 moles of a free tertiary amine, per mole of carbonate.

2. A process as claimed in claim 1, wherein the reaction is carried out in an aliphatic halohydrocarbon or an aprotic-polar solvent.

3. A process as claimed in claim 2, wherein the reaction is carried out in methylene chloride, tetrahydrofuran, dimethylformamide of dimethyl sulfoxide.

4. A process as claimed in claim 1, wherein an excess of methylamine is avoided.

* * * * *